(12) United States Patent
Murata et al.

(10) Patent No.: US 12,329,596 B2
(45) Date of Patent: Jun. 17, 2025

(54) DENTAL TREATMENT ASSISTANCE DEVICE, DENTAL TREATMENT ASSISTANCE SYSTEM, DENTAL TREATMENT ASSISTANCE METHOD, DENTAL TREATMENT ASSISTANCE PROGRAM, AND DENTAL PRODUCT SALES PROMOTION DEVICE

(71) Applicant: KURARAY NORITAKE DENTAL INC., Kurashiki (JP)

(72) Inventors: Naofumi Murata, Chiyoda-ku (JP); Satoshi Yamaguchi, Chiyoda-ku (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 774 days.

(21) Appl. No.: 17/284,294

(22) PCT Filed: Oct. 10, 2019

(86) PCT No.: PCT/JP2019/039984
§ 371 (c)(1),
(2) Date: Apr. 9, 2021

(87) PCT Pub. No.: WO2020/075796
PCT Pub. Date: Apr. 16, 2020

(65) Prior Publication Data
US 2021/0338400 A1    Nov. 4, 2021

(30) Foreign Application Priority Data

Oct. 11, 2018  (JP) .................................. 2018-192868

(51) Int. Cl.
*A61C 19/00*     (2006.01)
*G06T 19/00*     (2011.01)
(Continued)

(52) U.S. Cl.
CPC ............ *A61C 19/00* (2013.01); *G06T 19/006* (2013.01); *G16H 30/20* (2018.01); *G16H 40/60* (2018.01); *G06T 2207/30036* (2013.01)

(58) Field of Classification Search
None
See application file for complete search history.

(56) References Cited

U.S. PATENT DOCUMENTS 11,583,371 B1 * 2/2023 Salmassy ............. A61C 8/0089
2013/0323674 A1 * 12/2013 Hakomori ............. A61B 1/043
433/29
(Continued)

FOREIGN PATENT DOCUMENTS

| CN | 105662584 A | 6/2016 |
| CN | 108814641 A | 11/2018 |

(Continued)

OTHER PUBLICATIONS

International Search Report issued on Nov. 26, 2019 in PCT/JP2019/039984 filed on Oct. 10, 2019, 2 pages.

(Continued)

*Primary Examiner* — James A Thompson
(74) *Attorney, Agent, or Firm* — Oblon, McClelland, Maier & Neustadt, L.L.P.

(57) ABSTRACT

A dental treatment assistance device includes a display, an input part into which input information on at least one of a use purpose and a use product is input, a memory that stores product information and process procedure information for a purpose of each product, a product information acquiring part that acquires the product information and the process procedure information corresponding to the input information input from the input part; and a display image control (Continued)

part that displays a predetermined process procedure selected from the process procedure information on the display.

21 Claims, 10 Drawing Sheets

(51) Int. Cl.
  *G16H 30/20* (2018.01)
  *G16H 40/60* (2018.01)

(56) References Cited

U.S. PATENT DOCUMENTS

| | | |
|---|---|---|
| 2016/0151117 A1 | 6/2016 | Gibbs et al. |
| 2016/0220105 A1 | 8/2016 | Duret |
| 2018/0036100 A1* | 2/2018 | Kim ................... A61B 5/4547 |
| 2018/0168781 A1* | 6/2018 | Kopelman ............ A61B 34/10 |
| 2018/0263583 A1 | 9/2018 | Rintamaki et al. |
| 2019/0150825 A1 | 5/2019 | Kambara et al. |
| 2020/0143541 A1* | 5/2020 | Wang ....................... G06T 3/40 |

FOREIGN PATENT DOCUMENTS

| | | |
|---|---|---|
| CN | 109561820 A | 4/2019 |
| EP | 3 028 661 A2 | 6/2016 |
| EP | 3 375 373 A1 | 9/2018 |
| EP | 3 456 240 A1 | 3/2019 |
| JP | 2005-267115 A | 9/2005 |
| JP | 2009-195495 A | 9/2009 |
| JP | 2011-212367 A | 10/2011 |
| JP | 2012-203572 A | 10/2012 |
| JP | 2015-100437 A | 6/2015 |
| JP | 2017-200537 A | 11/2017 |
| JP | 2017-202301 A | 11/2017 |
| JP | 201/-153636 A | 10/2018 |
| KR | 10-2016-0066522 A | 6/2016 |
| KR | 10-2018-0106906 A | 10/2018 |
| KR | 10-2019-0004797 A | 1/2019 |
| WO | WO 2017/195820 A1 | 11/2017 |

OTHER PUBLICATIONS

Extended European Search Report issued Jun. 1, 2022 in European Patent Application No. 19870774.7, 12 pages.

* cited by examiner

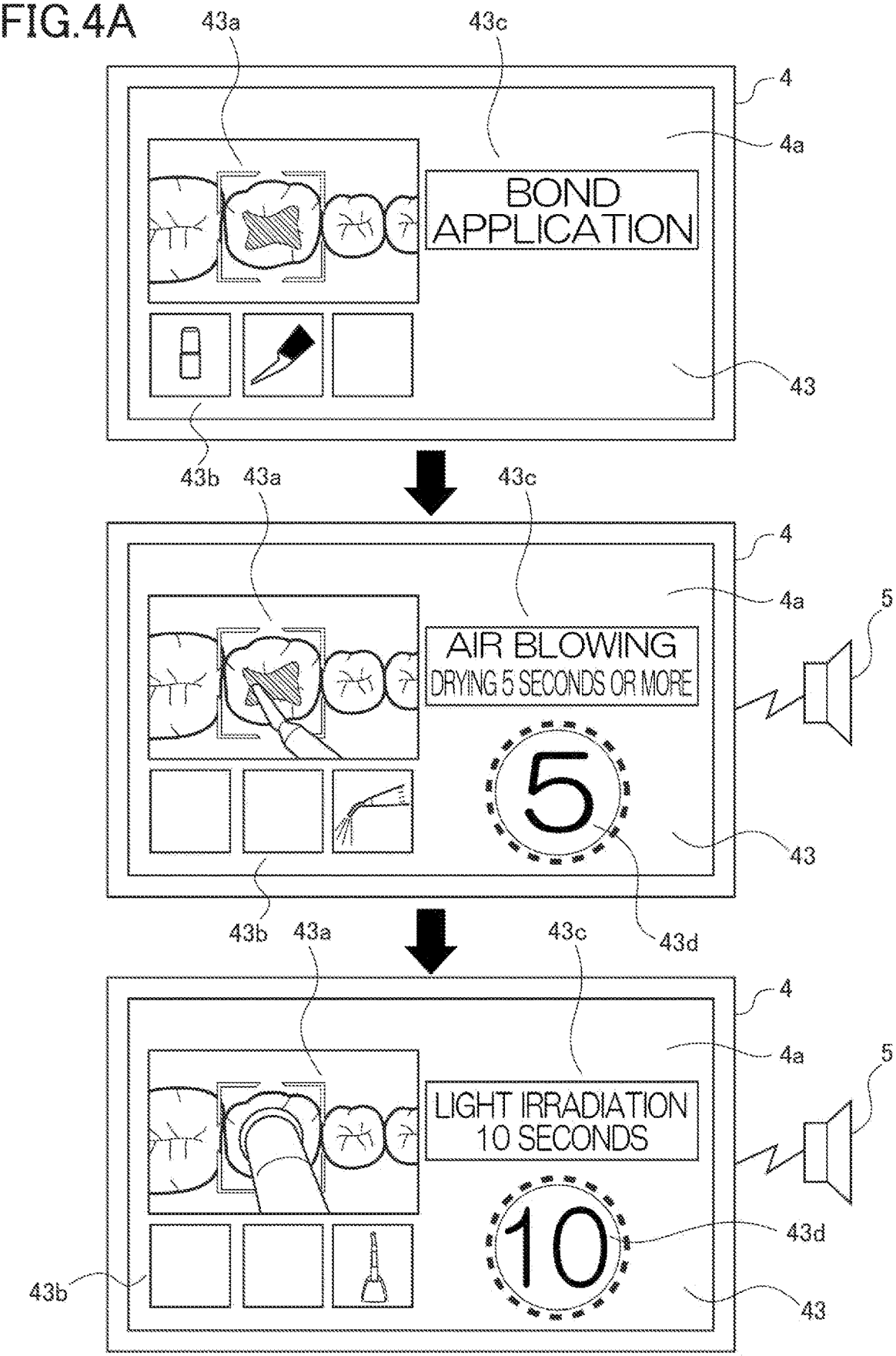

FIG.4B
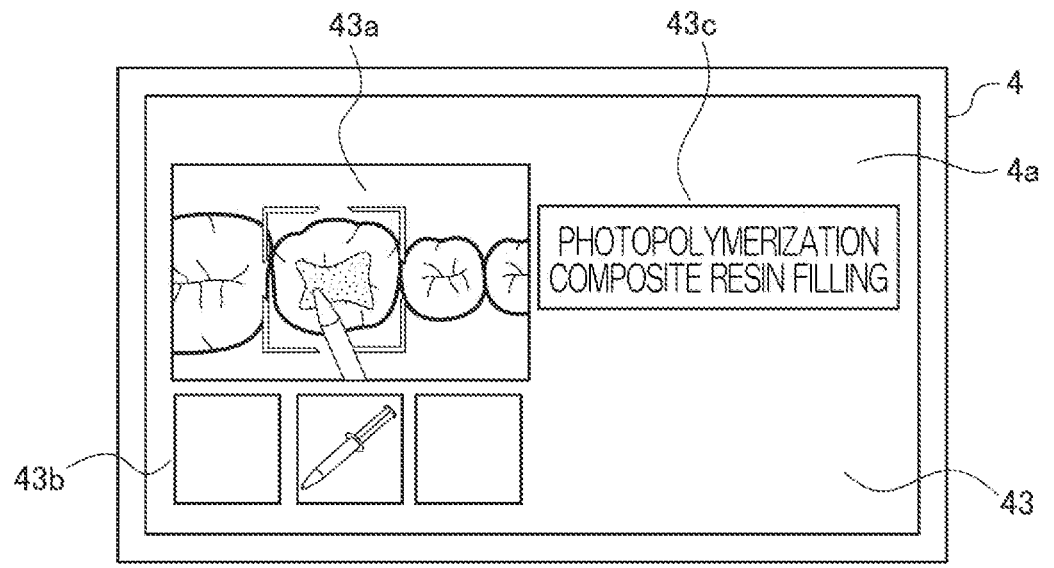
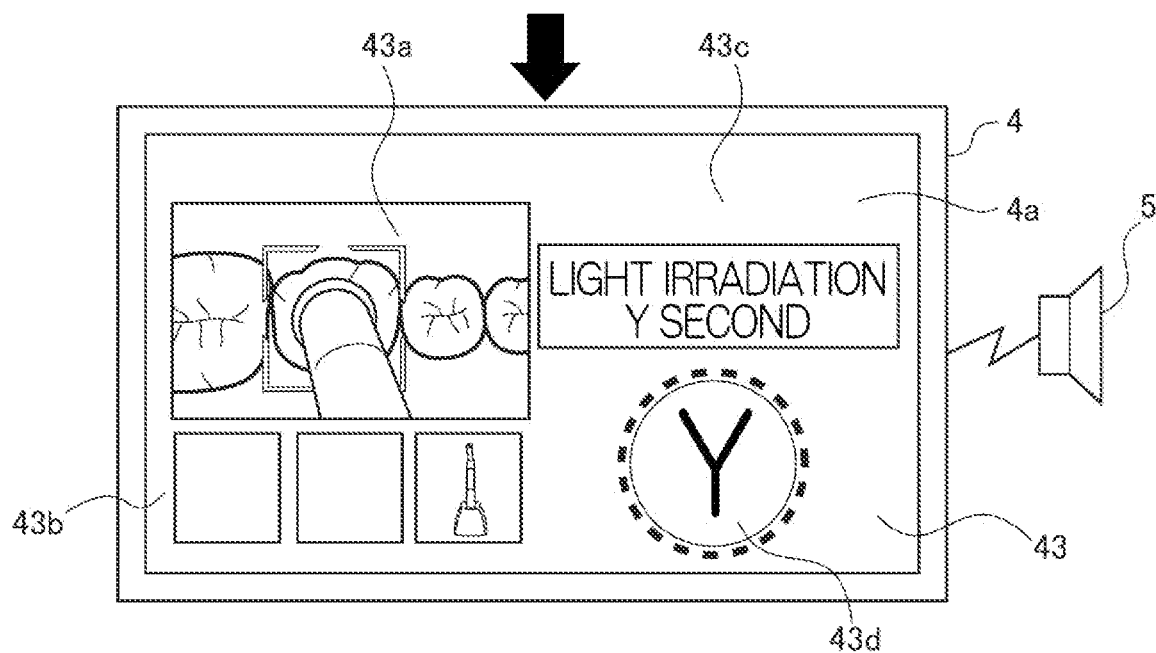

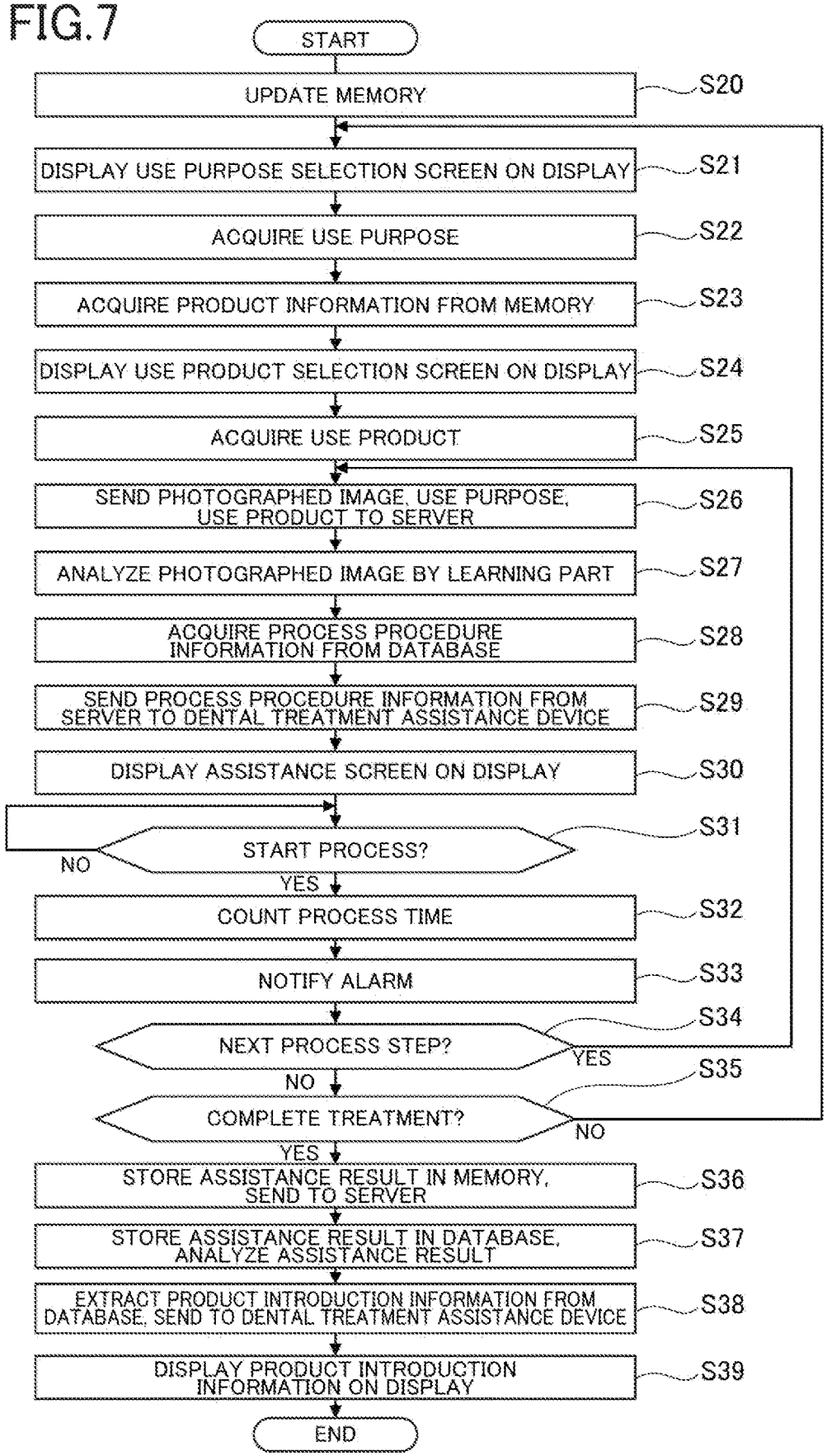

DENTAL TREATMENT ASSISTANCE DEVICE, DENTAL TREATMENT ASSISTANCE SYSTEM, DENTAL TREATMENT ASSISTANCE METHOD, DENTAL TREATMENT ASSISTANCE PROGRAM, AND DENTAL PRODUCT SALES PROMOTION DEVICE

CROSS-REFERENCE TO RELATED APPLICATION

The present application is based on and claims priority to Japanese Patent Application No. 2018-192868, filed on Oct. 11, 2018, the disclosure of which is hereby incorporated by reference in its entirety.

TECHNICAL FIELD

This disclosure relates to a dental treatment assistance device, a dental treatment assistance system, a dental treatment assistance method, a dental treatment assistance program, and a dental product sales promotion device.

BACKGROUND ART

In a dental clinical practice, a restorative filling material and a crown restoration material are generally used for restoration of tooth structures damaged by a dental caries and breakage, for example. The restorative filling material is, for example, a filling composite resin and a composite resin for constructing an abutment. The crown restoration material is, for example, a metal alloy, ceramics, and a resin material. Additionally, an adhesive material such as a bond and a cement for adhering the restorative filling material and the crown restoration material with the tooth structures is generally used. A typical treatment procedure example includes application of a bond to damaged tooth structures, polymerization and curing by optical irradiation for a predetermined time with an optical irradiation device after drying for a predetermined time with air blowing, filling of a filling composite resin, and polymerization and curing by optical irradiation for a predetermined time with an optical irradiation device. A dental hygienist attends to such a dental treatment by a dentist, and supports the dentist by passing a dental material to be used, and mixing a chemical agent, for example. However, the usage differs depending on each product. It is therefore necessary for a dentist and the like to memorize the usage in advance. When it is not possible to memorize all the usages, it may be possible to check the procedure with a specification, the Internet, and an application, for example. However, it is inconvenient to check the procedure at every treatment, which may make a smooth treatment and support difficult. When a new product is introduced, the usage is changed to new usage, so that it becomes necessary to rememorize the usage. For this reason, there are quite a few dentists who are passive in introducing a new product.

It is also difficult for a dental hygienist to directly observe an oral cavity of a treatment target together with a dentist, and to check which step is now taking in a treatment, so that a support operation may be affected.

On the other hand, a dental practice assistance system using an image of an oral cavity photographed by a camera is developed (see JP2017-200537A, for example). The treatment assistance system described in Patent Literature 1 is configured to superimpose an image of nerves, blood vessels, implants, and the like acquired based on a CT image of a person to be treated onto a real image of an oral cavity photographed by a camera, and display the superimposed image on a head mount display mounted by a dentist, to assist a treatment by the dentist.

However, the conventional technique described in Patent Literature 1 provides no guidance for a use procedure of a product required for a treatment step, and the use procedure still must rely on a memory of a dentist and the like.

SUMMARY

The present disclosure has been made in view of the above circumstances, and therefore, an object of the present disclosure is to provide appropriate guidance for process procedure corresponding to a treatment step without relying, on a human memory of a human to enable a more appropriately assistance of a dental treatment.

In order to achieve the object, a dental treatment assistance device includes a display, an input part into which input information at least one of a use purpose and a use product is input, a memory that stores product information and process procedure information for a purpose of each product, a product information acquiring part that acquires the product information and the process procedure information corresponding to the input information input from the input part, and a display image, control part that displays a predetermined process procedure selected from the process procedure information on the display.

BRIEF DESCRIPTION OF DRAWINGS

FIG. 4A is an explanatory drawing of an example of a flow of a display image onto the display of the dental treatment assistance device shown in FIG. 1.

FIG. 4B is an explanatory drawing of an example of a flow of a display image onto the display of the dental treatment assistance device shown in FIG. 1.

FIG. 7 is a flowchart illustrating an example of an operation of the dental treatment assistance system according to the fourth embodiment.

DESCRIPTION OF EMBODIMENTS

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

First Embodiment

Figure 1:
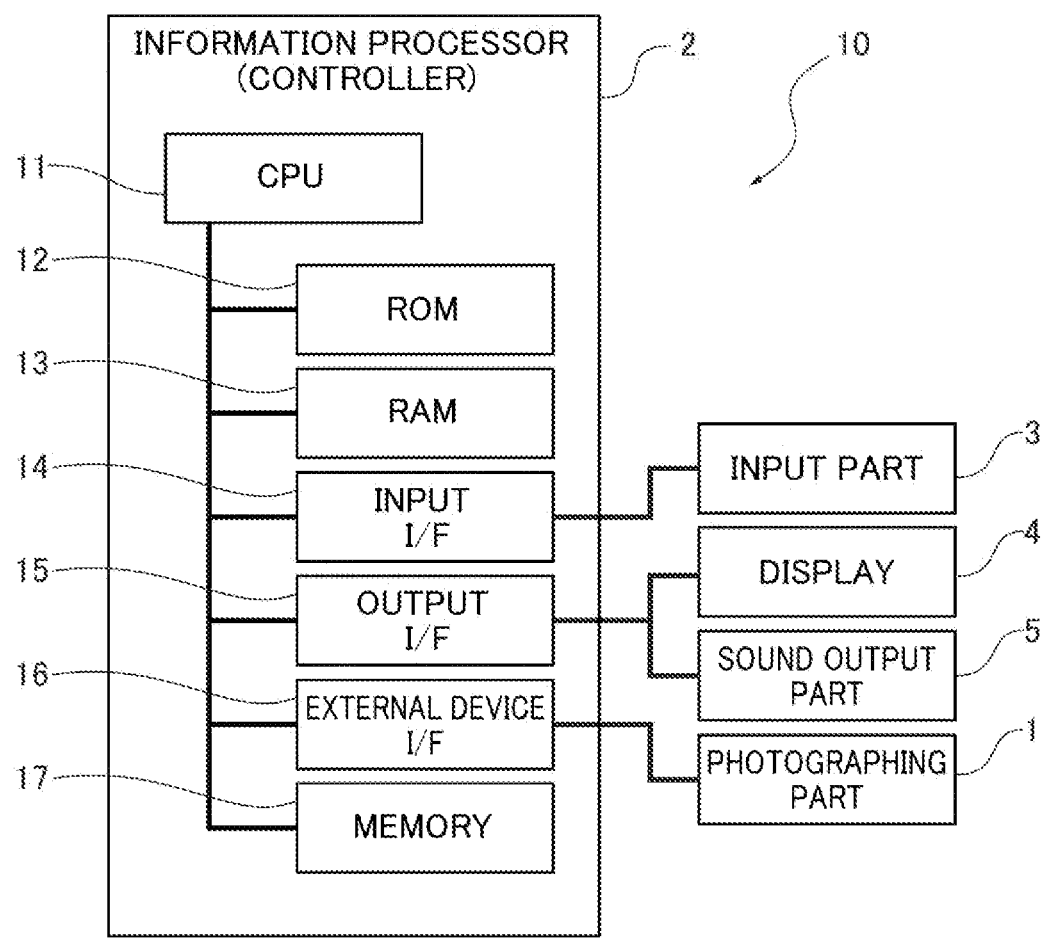
FIG. 1 is a schematic view showing a hardware configuration of a dental treatment assistance device according to a first embodiment of the present disclosure.

Hereinafter, a dental treatment assistance system according to a first embodiment of the present disclosure will be described with reference to the drawings. FIG. 1 is a schematic view showing a hardware configuration of a dental treatment assistance device 10 according to this embodiment. As shown in FIG. 1, the dental treatment assistance device 10 mainly includes a photographing part 1, an information processor (controller) 2, an input part 3, a display 4, and a sound output part 5. In addition to these, the dental treatment assistance device 10 may include a printer as an output, which prints a photographed image by the photographing part 1 and a dental treatment assistance result, and a communication device that communicates with an external device.

The photographing part 1 is a device that photographs an image of an oral cavity including a treatment target such as a tooth of a person to be treated. The photographing part 1 is not specifically limited, and appropriately includes a microscope, a wearable camera, a CCD camera, and a digital video camera fixed to an examination table, for example. The dental treatment assistance device 10 includes at least one photographing part 1, but may include a plurality of the same photographing parts 1 or a plurality of different photographing parts 1. When a plurality of photographing parts 1 are used, a treatment target and a treatment step can be detected in more detail and the treatment target can be three dimensionally displayed by photographing the treatment target with various angles and photographing conditions.

The photographing part 1 and the information processor 2 are wire connected by a connection cable or wireless connected by a wireless LAN such as Wi-Fi (registered trademark), for example. An image signal of the treatment target photographed by the photographing part 1 is output to the information processor 2 in real time. The photographed image may be a still image or a moving image. In this embodiment, the moving image is photographed, and is output to the information processor 2 in real time.

As illustrated in FIG. 1, the hardware configuration of the information processor 2 includes a CPU 11, a ROM 12, a RAM 13, an input I/F (interface) 14, an output I/F 15, an external device I/F 16, and a memory 17. However, the hardware configuration of the information processor 2 is not limited to such a configuration.

The CPU 11 is a central processing unit to control the entire operation of the dental treatment assistance device 10. The ROM 12 is a read-only memory to store, for example, a dental treatment assistance program and a control program, which are executed by the CPU 11. The RAM 13 is a random access memory which is used as a work area of the CPU 11. That is, the CPU 11 executes the dental treatment assistance program stored in the ROM 12 to operate the dental treatment assistance device 10 with the RAM 13 as a work area.

The memory 17 is composed of a recording medium such as a hard disk and a flash memory. The input I/F 14 is an interface to connect the input part 3 with the CPU 11. The output I/F 15 is an interface to connect the display 4 and the sound output part 5 with the CPU 11. The external device I/F 16 is an interface to connect the external device with the CUP 11. In this embodiment, the photographing part 1 is connected with the CPU 11.

The memory 17 previously stores product information of various products, process procedure (use procedure) information for each product, and the like, as various information items required for a dental treatment assistance process. The memory 17 also stores information in which the photographed image of the treatment state photographed by the photographing part 1 is associated with an assistance result, for example. The memory 17 also temporarily stores, for example, a calculation result in each part.

The product information includes a product name, a name of a dental material contained in a product, a component of each dental material, a usable purpose, and information on a tool and a device for use in each purpose. These are classified according to products to be stored in the memory 17. The memory 17 also stores, for example, introduction information of a product such as a list of a correspondence between a purpose and a usable product, an introduction document of a product, and a URL of a product-related site, as the product information.

The product may be a product composed of one dental material or may be a kit product composed of a plurality of dental materials, The dental material includes a bond a cement, a filling composite resin, a composite resin for constructing an abutment, a metal alloy, ceramics, a resin hardened material, a plaster material, a burying agent, a grinding agent, and an adhesive. However, the product is not limited thereto.

Even one dental material has various purposes. For example, "CLEARFIL (registered trademark) UNIVERSAL BOND" manufactured by Kuraray Noritake Dental Inc., can be used for filling restoration of a cavity with a dental filling composite resin (hereinafter, referred to as CR), cavity sealing, a medical activity of an exposed root surface, repair of a crown restoration with CR, post implanting, and other various treatments and medical activities. The tool and the device to be used, and also a separately used dental material (for example, CR) may differ according to purposes. Accordingly, the dental treatment assistance requires the information on these purposes and the tool for use in each purpose, for example. The memory 17 stores a process step for each purpose of each product, a tool and a device for use in each process step, a processing time in each process step, and the like.

The assistance result is meant to be an actual treatment process and treatment result using the dental treatment assistance device 10. The memory 17 stores information on a used product and its purpose and information on a performance result of an actual treatment process in a treatment step and a process step (for example an actual time when 10 seconds of a drying time is actually required although a general drying time is 5 seconds), as the assistance result.

In this embodiment, such an information processor 2 is composed of a desktop personal computer (PC). Note that the information processor 2 is not limited to the desktop PC, and may be composed of a laptop PC in which the display 4 is integrated. The information processor 2 is also not limited to a PC, for example, and may be composed of a smartphone, a cellular phone, or a portable information device of a tablet terminal in which the display 4 is integrated.

The input part 3 is a device for inputting a character, a number, and various instructions, for example, and is operated by a dentist, a dental hygienist, and the like. The input part 3 includes a keyboard, a mouse, and a tenkey. When the display 4 is a touch panel display, a touch panel screen operates as the input part 3. The input part 3 receives, for example, the input of the input information on a use purpose (content of treatment step), a use product (dental material), and the like by a dentist and a dental hygienist, for example. The signal of the input information is output to the information processor 2.

The display 4 is a device for displaying an input screen of the use purpose and the use product, the photographed image by the photographing part 1, and the process procedure of the dental material. The display 4 preferably includes a liquid crystal display and an organic EL display. When a portable information device is used as the information processor 2, a touch panel display is used as the display 4. However, when a PC is used as the information processor 2, the touch panel display may be also used as the display 4.

At least one display 4 is provided. However, a plurality of displays 4 may be provided. For example, when both of the display 4 for a dentist and the display 4 for a dental hygienist are provided, the dentist and the dental hygienist can perform a treatment and a support in the respective working positions while visually recognizing the displays 4 disposed in clearly visible places. When a plurality of the displays 4 are provided or a large monitor is used, a person in addition to a dentist and a dental hygienist can visually recognize the treatment state according to the use procedure. Thus, such a plurality of displays and a large monitor can be appropriately used in a class, a public treatment, a demonstration of a product introduction, and the like.

The display of the head mount display may be the display 4 of the present embodiment. When a dentist mounts such a head mount display, the dentist can perform a treatment while checking the process procedure displayed on the display 4 and observing an oral cavity through the head mount display. A photographed image corresponding to a visual line of the dentist and the like can be acquired by attaching a wearable camera to the head mount display as the photographing part 1.

The sound output part 5 is a device that outputs a notification sound for a predetermined notification to a dentist, a dental hygienist, and the like. The sound output part 5 includes a speaker and a buzzer. The notification sound output from the sound output part 5 is not specifically limited, and may be a buzzer and an alarm that notify the start and the end of the drying time and the optical irradiation time of the dental material. A sound and a voice that count a time may be produced, and passage of a time may be notified by the sound and the voice. The contents of the process step such as "PLEASE APPLY BOND" and "PLEASE IRRADIATE" may be notified by the voice.

Figure 2:
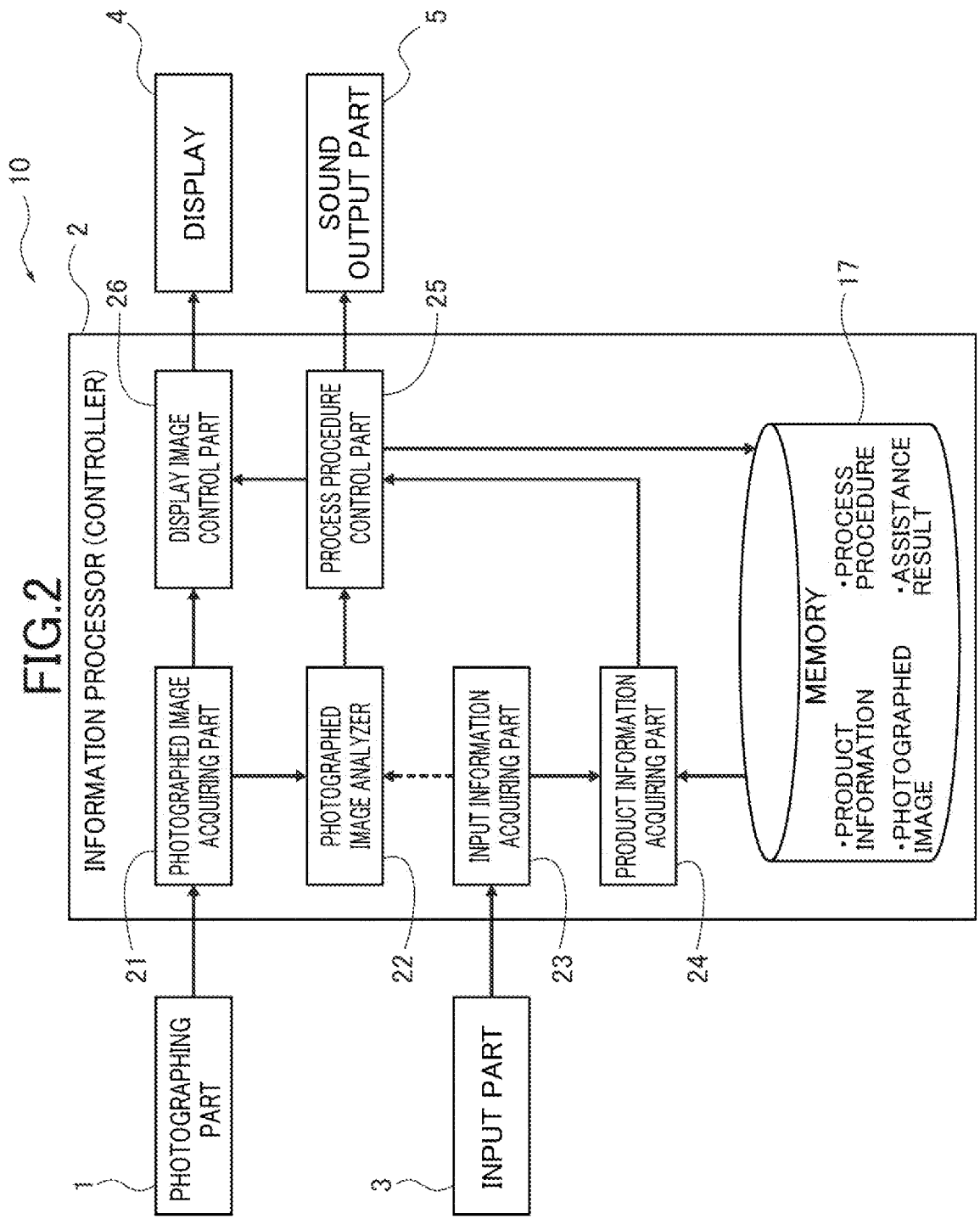
FIG. 2 is a functional block diagram of the dental treatment assistance device shown in FIG. 1.

Next, the operation of the information processor 2 that controls the entire operation of the dental treatment assistance device 10 will be described with reference to the operation block diagram of FIG. 2. As illustrated in FIG. 2, the information processor 2 operates as a photographed image acquiring part 21, a photographed image analyzer 22, an input information acquiring part 23, a product information acquiring part 24, a process procedure control part 25, and a display image control part 26.

The photographed image acquiring part 21 converts the image signal input in real time from the photographing part 1 into a digital signal, and sends the photographed image to which an appropriate image process is performed to the photographed image analyzer 22 and the display image control part 26.

The photographed image acquiring part 21 may control the photographing part 1 to enlarge a vicinity of a detected treatment target for photographing, and may control the photographing part 1 by using an object tracking technique to track the detected treatment target for photographing. The photographed image acquiring part 21 may be configured to automatically detect the treatment target by the photographing part 1 with, for example, an autofocusing operation and an object recognition operation of the photographing part 1 to focus, enlarge, and track the treatment target for photographing.

The photographed image analyzer 22 analyzes the photographed image from the photographed image acquiring part 21 to detect the treatment target such as a dental caries, a cavity, and a root canal. For example, the photographed image analyzer 22 performs an object recognition process such as extraction of a feature amount and pattern matching to detect a dental caries, a cavity, and the like, as the treatment targets. In this case, the photographed image analyzer 22 may detect the treatment target according to the purpose input by the input part 3. For example, when the purpose is the filling restoration and the sealing of the cavity, the photographed image analyzer 22 detects the cavity from the photographed image as the treatment target. To be more specific, for example, a tooth designated by a mouse clicking operation and a touch panel touching operation with a dentist and the like on the photographed image displayed on the display 4 may be detected as the treatment target.

The photographed image analyzer 22 analyzes the photographed image to identify a treatment step which takes (will take) to the treatment target by a dentist based on the analysis result and the input information. The information of the detected treatment target and the information of the recognized treatment step are sent to the process procedure control part 25. The information processor 2 may include a learning part having an artificial intelligence (AI). The information processor 2 may perform amore detailed advanced treatment assistance based on the information analyzed by the photographed image analyzer 22 and previously stored teaching data. For example, the photographed image analyzer 22 identifies the treatment target by the image analysis, and inputs the feature amount and the input information of the treatment target to the learning part. The learning part uses, as teaching data, data in which the feature amount presenting a dental caries, a cavity, a root canal, and the like of various conditions which require a treatment is associated with an actual treatment step, a process step, and a product information to be used, to the dental caries, the cavity, the root canal, and the like of the various conditions. Then, the learning part uses a machine learning algorism such as a neutral network based on the feature amount and the input information of the input treatment target, identifies the treatment step by determining a shape of the cavity of the treatment target, and outputs the corresponding process procedure and the use material. The photographed image analyzer 22 may present a more appropriate use material according to the treatment step based on die output from the learning part to a dentist, for example. The learning part may discriminate a tool (for example, brush and instrument) to be used by a dentist and a material (for example, property and color) to be used based on the analysis result of the photographed image with the data in which the treatment step is associated with the tool (for example, brush and instrument) and the material (for example, property and color), and may determine which process step of the treatment step is taking.

The input information acquiring part 23 acquires the input information on the use purpose, the use product, and the like input from the input part 3. The product information acquiring part 24 acquires the corresponding product information and the process procedure information corresponding to the use purpose from the memory 17 based on the information on the use purpose and the use product acquired by the input information acquiring part 23. The acquired product information and process procedure information are sent to the process procedure control part 25.

The process procedure control part 25 selects an arbitrary process procedure corresponding to the input information from the process procedure information acquired by the product information acquiring part 24. In the first embodiment, the process procedure control part 25 selects the process procedure corresponding to the treatment step analyzed by the photographed image analyzer 22 in addition to the input information. The process procedure control part 25 controls the display image control part 26 to display the selected process procedure information on the display 4. The process procedure control part 25 counts a processing time upon the start of the process in, the process step (for example, drying step and optical irradiation step) which requires the counting of the processing time, and outputs, for example, an alarm sound from the sound output part 5 when it reaches a predetermined processing time.

The process procedure control part 25 stores the data in which the photographed image is associated with the assistance result in the memory 17 when the treatment is completed. The assistance result includes the information on the product information such as a name of a used product and the use purpose and the information on a performance result of an actual treatment process in a treatment step and a process step (for example, actual drying time and optical irradiation time, and process when process different from predetermined process is performed).

The process procedure control part 25 controls the display image control part 26 according to needs to display introduction information of a product on the display 4. The screen of the introduction information may be a screen on which the detailed instruction of the use product is described or a screen on which a use instruction of another production having the same purpose as the use product is described. By visually recognizing these screens, a dentist and a dental hygienist can again recognize the use procedure of the product, get to know another use purpose of the product, for example, and become aware of information on a more appropriate product to the use purpose.

As the screen of the introduction information, a screen including a URL of a site in which the information of these products is released and a URL of a site in which a moving image of a use example of a product is released. For example, a dentist is guided to that site by clicking such a URL, so that the dentist can become aware of the more detailed information and the use example of the product, and can consider the purchase of the product.

Figure 3:
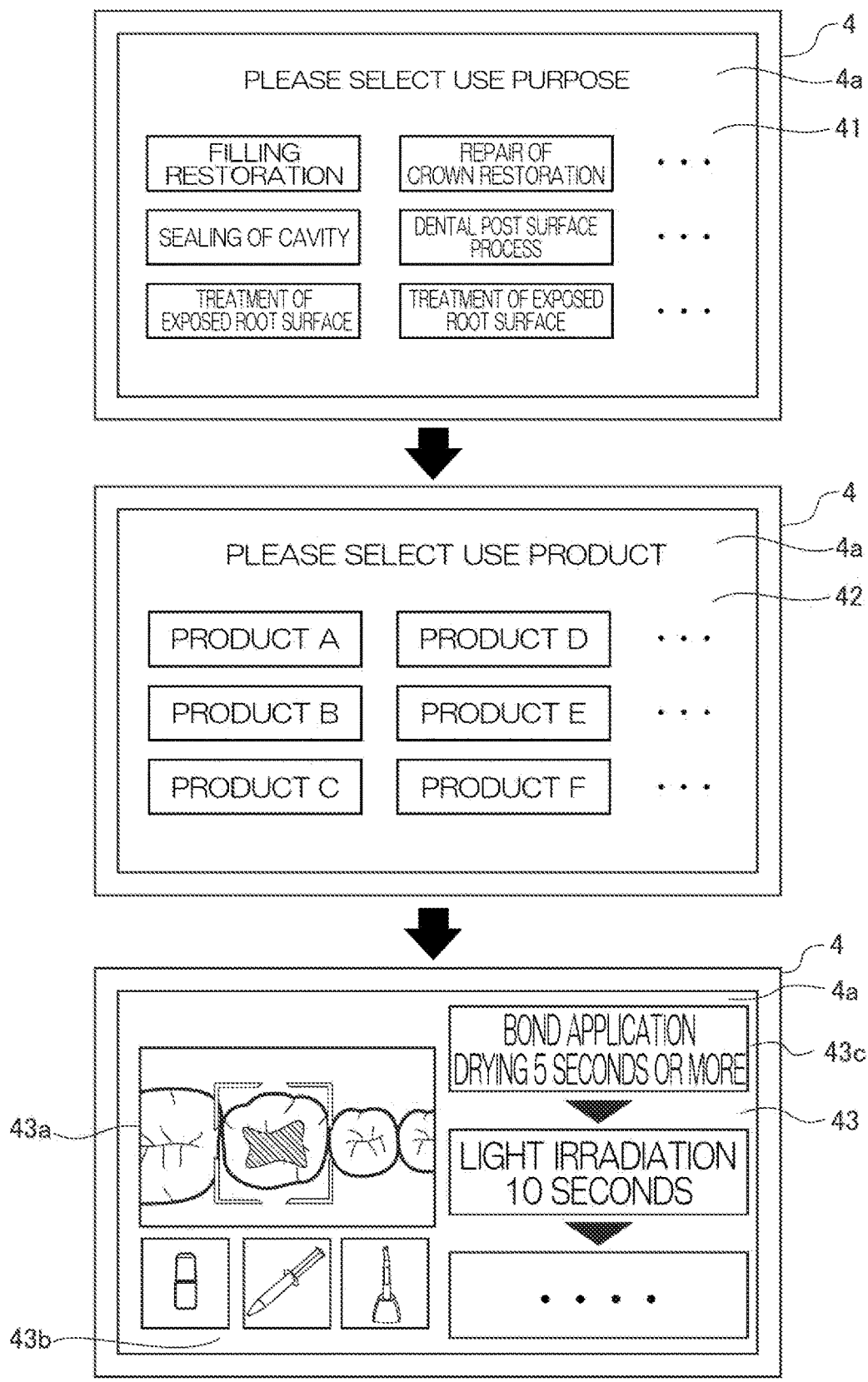
FIG. 3 is an explanatory drawing of an example of a flow of a display image onto a display of the dental treatment assistance device shown in FIG. 1.

The display image control part 26 creates an image to be displayed on a display surface 4*a* (refer to FIG. 3) of the display 4, for example, a use purpose selection screen 41, a use product selection screen 42 illustrated in FIG. 3, and an assistance screen 43 illustrated in FIGS. 4A, 4B. The assistance screen 43 includes a photographed image display area 43*a* that displays a real time photographed image by the photographing part 1, a material display area 43*b* that displays an image of a dental material and a tool to be used, and a process procedure display area 43*c* that displays each step of the process procedure according to the treatment step. While counting the processing time, a counter image 43*d* (refer to FIG. 4A) may be displayed on the process procedure display area 43*c*.

Figure 5:
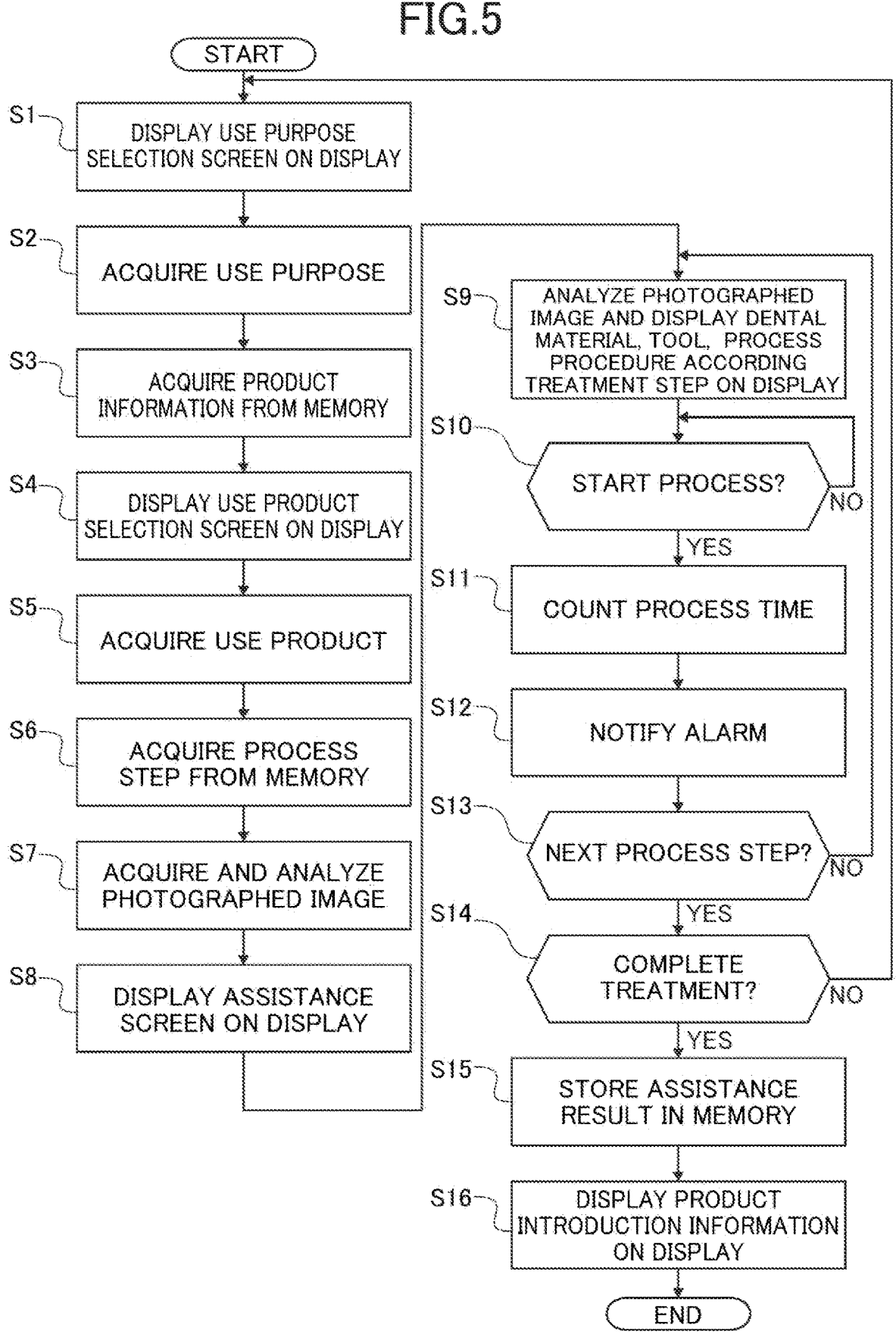
FIG. 5 is a flowchart showing an example of an operation of the dental treatment assistance device according to the first embodiment.

One example of the dental treatment assistance process (dental treatment assistance method, dental treatment assistance program) which is performed by the above described dental treatment assistance device 10 will be described with reference to the explanation drawings of the flow of the display image in FIGS. 3, 4A, 4B and the flowchart of FIG. 5. In this case, a situation in which a dental hygienist supports a treatment by a dentist while visually recognizing the image displayed on the display surface 4*a* of the display 4 is expected.

The dental treatment assistance device 10 is activated by starting a dental treatment assistance program in the PC as the information processor 2, and the photographing part 1 starts photographing an oral cavity of a person to be treated.

Then, the display image control part 26 displays on the display surface 4*a* of the display 4 the use purpose selection screen 41 on which the list of use purposes is displayed, as illustrated in the upper view of FIG. 3 (Step S1). For example, a dental hygienist can select a use purpose by the mouse clicking operation and the touch panel touching operation on a predetermined purpose of the use purpose selection screen 41. The input information acquiring part 23 acquires the information of the selected use purpose (Step S2). In this case, "FILLING RESTORATION" is selected.

The product information acquiring part 24 acquires the product information (in this case, list of names, for example) corresponding to the use purpose from the memory 17 according to the use purpose acquired by the input information acquiring part 23 (Step S3). Then, the display image control part 26 displays the use product selection screen 42 on which the list of the use products is displayed, as illustrated in the center view of FIG. 3 (Step S4). The input information acquiring part 23 acquires the information of the use product selected by a dental hygienist and the like from the use product selection screen 42 (Step S5). In this case, a product A is selected.

In this embodiment, the use purpose is previously selected, and then the product is selected. However, it is not limited to this configuration. The product may be previously selected, and then the use purpose may be selected from the purposes displayed according to the product. Only the use purpose may be input, and the product according to the use purpose may be automatically selected. Only the use product may be selected, and the purpose of the use product may be identified based on the treatment step identified by the analysis of the photographed image.

When the use purpose is selected, the product information acquiring part 24 acquires the product information corresponding to the acquired use product from the memory 17. More specifically, the product information acquiring part 24 acquires the process procedure information including the information of the process procedure of the product according to the use purpose, the necessary dentist material, the tool, and the like from the memory 17 (the above, Step S6).

With the above, the treatment assistance process according to the use purpose and the product is started. The photographed image (moving image) by the photographing part 1 is acquired by the photographed image acquiring part 21, is analyzed by the photographed image analyzer 22 to detect the treatment target. The photographed image analyzer 22 controls the photographing part 1 to enlarge and track the treatment target for photographing (the above, Step S7).

The photographed image by the photographing part 1 is displayed on the display 4 in real time by the display image control part 26. More specifically, the display image control part 26 displays the acquired photographed image on the photographed image display area 43*a*, as illustrated in the lower view of FIG. 3, displays the images of the dental material and the tool to be used on the material display area 43*b*, and displays the assistance screen 43 on which the image of the process procedure is displayed on the process procedure display area 43c on the display surface 4a of the display 4 (the above, Step S8). For example, an image near the treatment target and an enlarged image of the treatment target may be displayed on the photographed image display area 43a. When a plurality of photographing parts 1 are used, one or more photographed images by these may be appropriately selected to be displayed according to needs.

A dental hygienist can confirm the treatment step which is taking by a dentist by visually recognizing the photographed image displayed on the photographed image display area 43a of the assistance screen 43. The dental hygienist can also confirm the necessary dental material and tool by visually recognizing the material display area 43b. The dental hygienist can also confirm the specific step of the process procedure by visually recognizing the process procedure display area 43c. Accordingly, the dental hygienist can more appropriately and smoothly perform the assistance of the treatment such as the preparation of the tool as well as the preparation and the mixing of the dental material.

Next, the photographed image analyzer 22 analyzes the photographed image to detect the specific process step of the treatment step by a dentist. The process procedure control part 25 selects the dental material, the tool, and the process according to the detected treatment step. The display image control part 26 displays the selected dental material and tool on the material display area 43b, and displays the detail of the process procedure on the process procedure display area 43c (the above, Step S9). In this case, the sound output part 5 may output a message such as the content of the step of the process procedure, for example, "PLEASE APPLY BOND TO CAVITY" with sound.

The photographed image analyzer 22 analyzes the photographed image to determine whether or not the process has started (Step S10). When the process has not started (NO in Step S10), the program waits until the process starts. When it is determined that the process has started (YES in Step S10), the program proceeds to Step S11. In the next Step S11, the process procedure control part 25 counts the processing time when the counting of the processing time is required. In this case, the display image control part 26 displays the counter image 43d on the process procedure display area 43c. When it reaches the processing time, the process procedure control part 25 outputs the alarm sound, the alarm message, and the like by controlling the sound output part 5 to notify the alarm (Step S12). With this notification of the alarm, not only a dental hygienist but also a dentist can clearly notice that it reaches the drying time, for example.

When a dentist performs the process in a time different front a processing time previously set by the selling source of the product, the process procedure control part 25 may store the actual processing time. For example, the set processing time may not be sufficient for drying and curing, and the processing time may be set to be longer than the set processing time based on the judgement of the dentist. In this case, by collecting the data of the actual processing time to be considered, such data can be referred for changing the process procedure to be a more suitable process procedure.

Next, in Step S13, it is determined whether or not there is a next process step. When there is a process step (NO in Step S13), the process proceeds to Step S9 to repeat the steps of Steps S9 to S12.

On the other hand, when all the process steps have been completed (YES in Step S13), the process proceed to Step S14 to determine whether or not the treatment has completed. When a completion instruction is input by a dental hygienist, for example, from the input part 3, it is determined that the treatment has been completed (YES in Step S14), and the process proceeds to Step S15.

On the other hand, when a continuation instruction is input from the input part 3 or a return instruction to the use purpose selection screen 41 is input, it is determined that the treatment continues (NO in Step S14), and the process returns to Step S1 to repeat the steps of Steps S1 to S13.

After the treatment is completed, in Step S15, the process procedure control part 25 stores the data in which the photographed image by the photographing part 1 is associated with the assistance result of the use product, the use purpose, the actual process step, and the like in the memory 17.

The process also proceeds to Step S16 according to needs, and the display image control part 26 displays the introduction information of the product on the display 4. As described above, the introduction information of the product or the information to guide to a purchase site may be displayed. Information to introduce another purpose of the product used at this time may be displayed. When a dentist uses a certain product only for a certain purpose, the introduction screen of another product for use in the same purpose may be displayed based on the assistance result accumulated in the memory 17. Advertisement information of a product may be displayed in a predetermined area of the display surface 4a as a so-called listing advertisement.

A specific example of the flow of the assistance screen 43 to be displayed on the display 4 will be described with reference to FIGS. 4A, 4B. In the upper view of FIG. 4A, as a bond application step is identified as the specific process step of the treatment step, the images of the bond material and the application tool are displayed on the material display area 43b, and "BOND APPLICATION" is displayed on the process procedure display area 43c as the process step.

The photographed image analyzer 22 detects the application of the bond by detecting the application tool and detecting the liquid surface of the bond from the photographed image. According to this detection, the display image control part 26 displays an air nozzle, the process step (air blowing), and the processing time (five seconds or more) on the assistance screen 43 for a next drying step, as illustrated in the center view of FIG. 4A. When the photographed image analyzer 22 detects, for example, air injection by an air nozzle from the photographed image, the process procedure control part 25 starts counting the processing time, and the display image control part 26 displays the counter image 43d, as illustrated in the center view of FIG. 4A. When it reaches the processing time, the process procedure control part 25 outputs the alarm sound from the sound output part 5.

When the photographed image analyzer 22 detects the completion of the drying process, the process proceeds to the assistance of the optical irradiation step. The display image control part 26 displays the optical irradiation tool, the process step (optical irradiation step), and the processing time (10 seconds) on the assistance screen 43, as illustrated in the lower view of FIG. 4A. When the photographed image analyzer 22 detects the optical irradiation, the process procedure control, part 25 starts counting the processing time and displaying the counter image 43d. When it reaches the processing time, the process procedure control part 25 outputs the alarm sound from the sound output part 5.

The upper view of FIG. 4B illustrates the assistance screen 43 in a filling step of a photopolymerization type dental filling composite resin, which is performed after the application of the bond. An image of the composite resin material to be used and the process step (photopolymerization composite resin filling) are displayed on the assistance screen 43. When the photographed image analyzer 22 detects the completion of the filling, the display image control part 26 displays the optical irradiation device, the process step (optical irradiation step), and the processing time (Y second) on the assistance screen 43, as illustrated in the lower view of FIG. 4B. In this case, the process procedure control part 25 also counts the processing time and outputs the alarm sound. Next, the process procedure control part 25 may display the assistance screen 43 of a polishing step, for example.

In the above, the dental treatment assistance device 10 of the present embodiment is used for the assistance of a dental hygienist. However, the device is not limited to such use. For example, a dentist can use such a device by himself or herself When there is no a dental hygienist, the dentist can perform the treatment while confirming the process step and the processing time by himself or herself.

Modified Example

A further simplified embodiment will be described as a modified example of the first embodiment. In the first embodiment, the assistance screen 43 corresponding to each process step of the treatment step is automatically displayed and the processing time is counted based on the treatment step detected by the image analysis of the photographed image analyzer 22. However, it is not limited thereto. For example, by only displaying the assistance screen 43 in the lower view of FIG. 3 on the display surface 4*a*, the dental material, the tool, and the process procedure for use can be immediately figured out. The assistance operations such as the receiving and passing of the tool, the mixing of the chemical agent, and the counting of the processing time can be performed according to the process step displayed on the process procedure display area 43*c* while confirming the treatment step by the real time photographed image displayed on the photographed image display area 43*a*. Alternatively, for example, a dentist can perform a medical action such as a treatment while confirming the display surface 4*a*. In this embodiment, it is not necessary to provide the photographed image analyzer 22, and it is possible to provide the faster dental treatment assistance device 10 having the further simplified configuration.

As another different embodiment (modified example), the product information acquiring part 24 may acquire the process procedure information corresponding to the input information from the memory 17 based on the input information of the use purpose, the use product, and the like input from the input part 3, and display the real time photographed image and the acquired process step side by side on the display 4. For example, a dentist can thereby perform the treatment and the treatment assistance while confirming the process step. A first process step of the process procedure information and the photographed image may be displayed side by side on the display 4 (for example, upper view of FIG. 4A). For example, a dentist can perform the treatment and the treatment assistance while confirming the photographed image and the process step. When the process step is completed, the screen is changed to a screen on which the next process step and the photographed image are displayed side by side by clicking a button "NEXT", for example, so that the dental treatment can be more appropriately assisted. In this case, it is not necessary to provide the photographed image analyzer 22.

As a further different embodiment (modified example), for example, a dental hygienist confirms the bond application by a dentist with the photographed image of the display 4, and selects "BOND APPLICATION" on the process procedure display area 43*c* of the assistance screen 43 in the lower view of FIG. 3 by the clicking operation or the touching operation. By this selection operation, the drying time may be counted, and the alarm sound may be notified. Alternatively, for example, a dental hygienist may sequentially select each process step of the process procedure display area 43*e* by the clicking operation to display the assistance screen 43 in FIG. 4A or FIG. 4B.

As described above, according to the first embodiment and the modified example, by inputting the input information of the use purpose or the use product, the suitable process procedure (use procedure) corresponding to the input information is selected, and is displayed on the display 4. For example, a dentist and a dental hygienist can thereby confirm the process procedure of the product. In the first embodiment and the modified example, the dental treatment assistance device 10 includes the photographing part 1 that photographs the oral cavity of the person to be treated including the treatment target, and the display image control part 26 displays a predetermined process procedure selected from the process procedure information and the photographed image by the photographing part 1 side by side on the display 4. For example, a dental hygienist can thereby clearly confirm the treatment target and the progress of the treatment step by a dentist by visually recognizing the photographed image displayed on the display 4. The dental hygienist can more properly and smoothly perform the assistance operations such as the preparation and the receiving/passing of the dental material and the tool according to the process procedure displayed on the display 4 while visually recognizing the photographed image. Alternatively, for example, a dentist can perform the treatment and the like while visually recognizing the photographed image and the process procedure on the displays. Accordingly, the process procedure corresponding to the use purpose, the use product, or the treatment step can be appropriately guided without relying on a human memory. As a result, the dental treatment assistance device 10, the dental treatment assistance method, and the dental treatment assistance program capable of more appropriately assisting the dental treatment can be provided.

In the first embodiment, the dental treatment assistance device 10 further includes the photographed image analyzer 22 that detects the treatment target in the photographed image, and identifies the treatment step to the treatment target, and the process procedure control part 25 that selects the process procedure corresponding to the treatment step from the process procedure information. With this configuration, the process procedure (use procedure) corresponding to the progress of the treatment step can be displayed on the display 4 together with the photographed image. It becomes unnecessary for a dentist and the like to confirm the treatment step. A further appropriate process procedure corresponding to the process of the actual process step can be displayed, and the dental treatment can be more appropriately assisted.

In the first embodiment, the process procedure control part 25 counts the processing time when a predetermined step of the process procedure is performed, and notifies the alarm when it reaches the processing time. With this configuration, not only a dental hygienist but also a dentist can clearly notice the passage of the processing time, so that the assistance effect can be further improved.

In the first embodiment, the process procedure control part 25 can notify the process procedure with sound. With this configuration, not only a dental hygienist hut also a dentist can notice the process procedure with sound, so that the assistance effect can be further improved.

In the first embodiment, the process procedure control part 25 stores the input information, the product information, the process procedure, and the performance result of the process procedure in the memory 17. With this configuration, for example, a dentist can check the treatment state by confirming the assistance result after the completion of the treatment, so that the assistance result can be used for a feature treatment.

In the first embodiment, the process procedure control part 25 displays the introduction information of the used product or the introduction information of the product corresponding to the process procedure on the display 4 based on the assistance result. With this configuration, for example a dentist can figure out the purpose of the product and the like in more detail. Moreover, for example, the dentist can get to know the information of another product more suitable for the purpose, and can positively and smoothly introduce a new product. Furthermore, a distributor of a product can promote own product. Thus, the dental treatment assistance device 10 capable of contributing to the positive introduction and the sales promotion of the product can be provided.

The dental treatment assistance device 10 may include a learning part having an artificial intelligence (AI). With this learning part, the analysis of the photographed image, the specification of the treatment target and the treatment step, and the selection of the suitable treatment step can he performed with higher accuracy. The learning results are accumulated, and the advanced dental treatment assistance suitable for a user requirement can be performed by using the accumulated learning results.

Second Embodiment

Figure 5A:
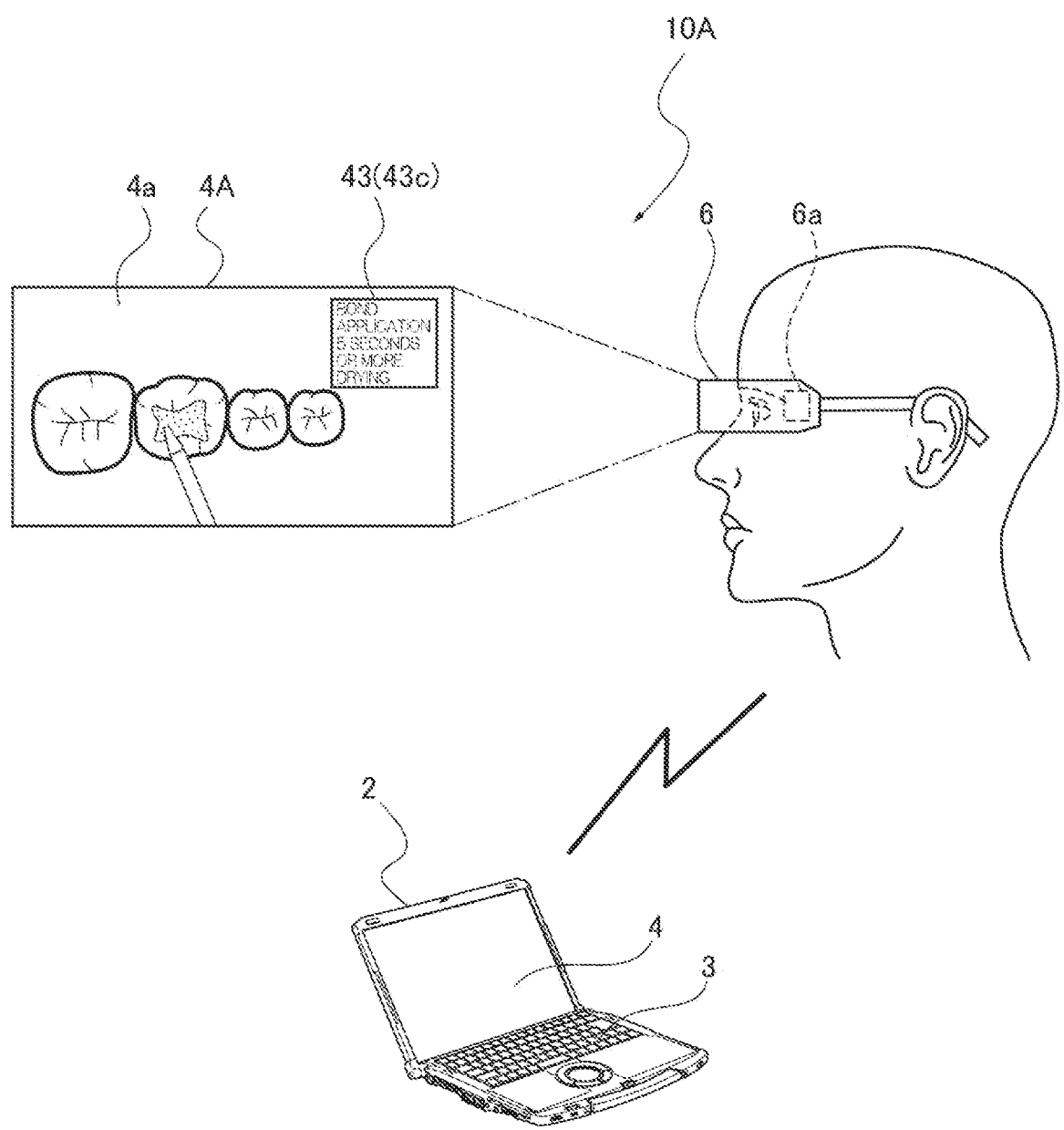
FIG. 5A is a schematic view showing a configuration of a dental treatment assistance device according to a second embodiment.

Next, a dental treatment assistance device 10A according to the second embodiment will be described with reference to FIG. 5A. As illustrated in FIG. 5A, the dental treatment assistance device 10A according to the second embodiment mainly includes a head mount display 6 and the information processor (controller) 2 of a PC. The information processor 2 includes the input part 3 and the display 4. As the configuration of the information processor 2 is similar to that of the first embodiment, the detailed description thereof will be omitted.

The head mount display 6 includes a control part 6a and a display 4A. The control part 6a includes a CPU, a ROM, a RAM, and a memory to control the entire operation of the head mount display 6. The control part 6a wire or wireless communicates with the information processor 2, and displays the information for the dental treatment assistance on the display 4A based on the control signal from the information processor 2.

The display 4A has a permeability capable of visually recognizing the treatment target while displaying the process procedure as the information for the dental treatment assistance. For example, an organic EL is suitably used as the display 4A. The information can be displayed on the entire surface of the display 4A, but the process procedure display area 43c on which the process procedure is displayed is provided in an upper right portion of a display surface 4a of the display 4A in this embodiment. The position of the process procedure display area 43c is not limited to the upper right portion of the display 4A, and the process procedure display area 43c can be provided in an appropriate position according to the process procedure and the treatment purpose, for example.

The head mount display 6 is not specifically limited as long as it includes the display 4A capable of displaying the information of the dental treatment assistance to enable the visual recognition of the treatment target through the display 4A. The configuration of the head mount display 6 is not specifically limited. For example, a google type, helmet type, or eyeglass type head mount display can be appropriately used. The head mount display is not limited to the one including the display 4A, 4B having the permeability capable of visually recognizing the treatment target while displaying the process procedure as the one in the second embodiment and an after described third embodiment. As another different embodiment, for example, a small display (monitor) such as a liquid crystal display may be attached to a leading end of an arm extending from the information processor fixed to a fastener to a head portion or a head portion, and the display may be disposed in a visual tiled of a mounted person. The mounted person thereby can visually recognize the process procedure and the like displayed on the display, and also can visually recognize the treatment target by further changing a viewpoint.

In the dental treatment assistance device 40A of the second embodiment as configured above, for example, a dentist (person to be mounted) mounts on his or her head the head mount display 6, and visually recognizes, for example, the tooth of the treatment target through the display 4A having a permeability. Next, when a dentist, a dental hygienist, or the like inputs the use purpose, the use product, and the like with the input part 3, the information processor 2 acquires the product information and the process procedure from the memory 17 based on these inputs, and sends the control signal of the display of the process procedure to the control part 6a of the head mount display 6. The control part 6a displays the process procedure on the display 4A based on the control signal. The process procedure may be sent from the information processor 2. The image and the like may be previously stored in the memory of the bead mount display 6, and the control part 6a may display the corresponding image and the like on the display 4A based on the control signal from the information processor 2.

As stated above, a dentist can perform the treatment and the like while visually recognizing the process procedure, the treatment target, and the like on the display 4A, and also confirming the process procedure displayed on the display 4A. In this case, for example, a dental hygienist can also confirm the process procedure by displaying the process procedure and the like on the display 4 of the information processor 2. For example, a dental hygienist may mount the head mount display 6 to assist a dentist while visually recognizing the treatment target and confirming the process procedure.

Third Embodiment

Next, a dental treatment assistance device 10B according to the third embodiment will be described with reference to FIG. 5B. The dental treatment assistance device 10B according to the third embodiment includes the basic configuration similar to that of the dental treatment assistance device 10A according to the second embodiment except that a head mount display 6B includes an information processor 2B instead of the control part 6a and a photographing part 1B. Accordingly, the same reference numbers as those of the dental treatment assistance device 10A according to the second embodiment illustrated in FIG. 5A are added, and the detailed description thereof will be omitted. Note that hereinafter the information processor 2B provided in the head mount display 6B is referred to as "MOBILE INFORMATION PROCESSOR 2B" to be distinguished from the information processor 2 of the PC.

Figure 5B:
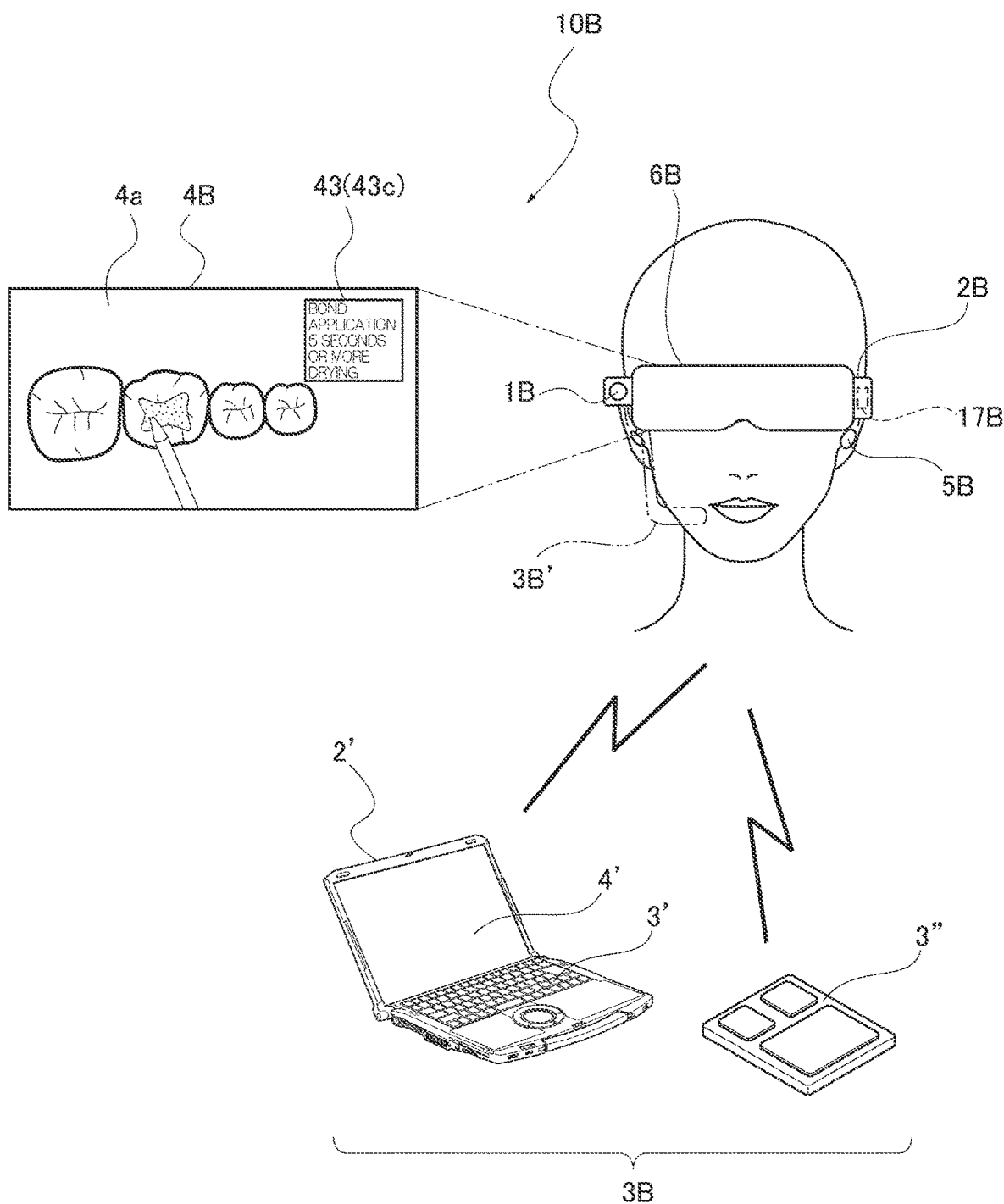
FIG. 5B is a schematic view showing a configuration of is dental treatment assistance device according to a third embodiment.

As illustrated in FIG. 5B, the dental treatment assistance device 10B according to the third embodiment mainly includes the head mount display 6B. The head mount display 6B includes the photographing part 1B, the mobile information processor 2B, an input part 3B'', a display 4B, and a sound output part 5B.

The photographing part 1B is arranged in a side part or an upper part of the display 4B to be able to photograph an oral cavity with a visual line of a person to be mounted. A device similar to that in the first embodiment, for example, a wearable camera is suitably used for the photographing part 1B. The photographed image corresponding to the visual line of the dentist, for example, can be acquired by the photographing part 1B. The photographed image is sent to an after described information processor 2', and is displayed on a display 4' of the information processor 2' and/or the display 4B of the head mount display 6B mounted by a dental hygienist, for example. For example, the dental hygienist thereby can confirm the treatment step which is taking by a dentist with the visual line of the dentist.

The mobile information processor 2B is fixed to a main body of the head mount display 6 (in this embodiment, temple of eyeglass type head mount display 6B). Alternatively, the mobile information processor 2B may be the separated mobile information processor 2B, which can be put in a pocket of a person to be mounted, to he wired or wireless connection with the main body.

The mobile information processor 2B is a compact information processor, and includes a CPU such as a microprocessor and a memory 17B such as a RAM, a ROM, and a recording medium. The mobile information processor 2B operates as the photographed image acquiring part 21, the photographed image analyzer 22, the input information acquiring part 23, the product information acquiring part 24, the process procedure control part 25, and the display image control part 26 (refer to FIG. 2) similar to the information processor 2 of the first embodiment.

The head mount display 68 is wired or wireless connection with the information processor 2' such as a PC and/or an input part 3'' such as a mouse capable of being operated by a hand and a foot of an operator. The information processor 2' is, for example, a PC including an input part 3' and a display 4'. The input part 3' is, for example, a keyboard, a mouse, and a tenkey. The input part 3' of the information processor 2' and the input part 3'' such as the mouse operate as the input part 38 of this embodiment. For example, a person to be mounted can thereby select the use purpose and the like by clicking the input part 3B on the various selection screens displayed on the display 4B. The input signal by this selection operation is output to the information processor 2B.

The memory 17B previously stores information required for the treatment assistance such as product information of various products and process procedure (use procedure) information for each purpose of a product. The information can be transferred from the information processor 2' to the memory 17B with the operation of the input part 3B (for example, copying and uploading operations). The memory 17B may store data in which the photographed image of the treatment state by the photographing part 1B is associated with the assistance result and the like. This information can be transferred from the memory 17B to the information processor 2' by the operation of the input part 3B (for example, copying and downloading operations).

The display 4B has a permeability which enables the treatment target to be visually recognized while displaying the process procedure. Similar to the display 4A of the second embodiment, for example, an organic EL is suitably used. The display surface 4a of the display 4B includes the process procedure display area 43c. The sound output part 5B outputs a predetermined notification to a person to be mounted. In this embodiment, the earphone type sound output part 5B which can be easily mounted on the ear of the person to be mounted is used. However, the sound output part SB is not limited thereto. For example, a speaker type sound output part may be used.

The dental treatment assistance device 10B according to the third embodiment of the above configuration obtains the effects similar to those of the first and second embodiments. That is, a dentist who mounts the head mount display 6B can perform the treatment and the like e visually recognizing the treatment target through the display surface 4a and confirming the process procedure displayed on the display 4A. For example, a dental hygienist can mount the head mount display 6B to assist a dentist while visually recognizing the treatment target and the process procedure. For example, the dental hygienist can perform the assistance while confirming the treatment target, the treatment step, and the process procedure with the same visual line as the dentist by displaying the photographed image by the photographing part 1, the process procedure, and the like on the display 4' of the information processor 2' and the display 4B of the head mount display 6B mounted by the dental hygienist, for example.

In the third embodiment, as the compact mobile information processor 2B is attached to the head mount display 6B or is put in a pocket, for example, the compact, light, and excellent portable dental treatment assistance device 10B can be provided. With the head mount display 6B which can be mounted on a head of a dentist, for example, and the input part 3' capable of being operated by a foot, for example, a dentist can freely perform the treatment and the assistance with both hands without using a hand for the operation and the like.

The dental treatment assistance device 10B according to the third embodiment includes the sound input part 3B' such as a microphone illustrated by the dashed line in FIG. 5B as an input part, and a sound analyzing software (sound analyzer) installed in the information processor 2B. With this configuration, for example, a dentist instructs the selection of the use purpose via voice (sound) from the sound input part, so that the sound analyzing software analyzes the sound, and the information processor 2B performs various processes according to the analysis results. Accordingly, for example, a dentist can freely and simply perform the treatment and the assistance without using a hand and a foot for the operation.

Fourth Embodiment

Next, a dental treatment assistance system 100 according to the fourth embodiment will be described with reference to the block diagram of FIG. 6 and the flowchart of FIG. 7.

Figure 6:
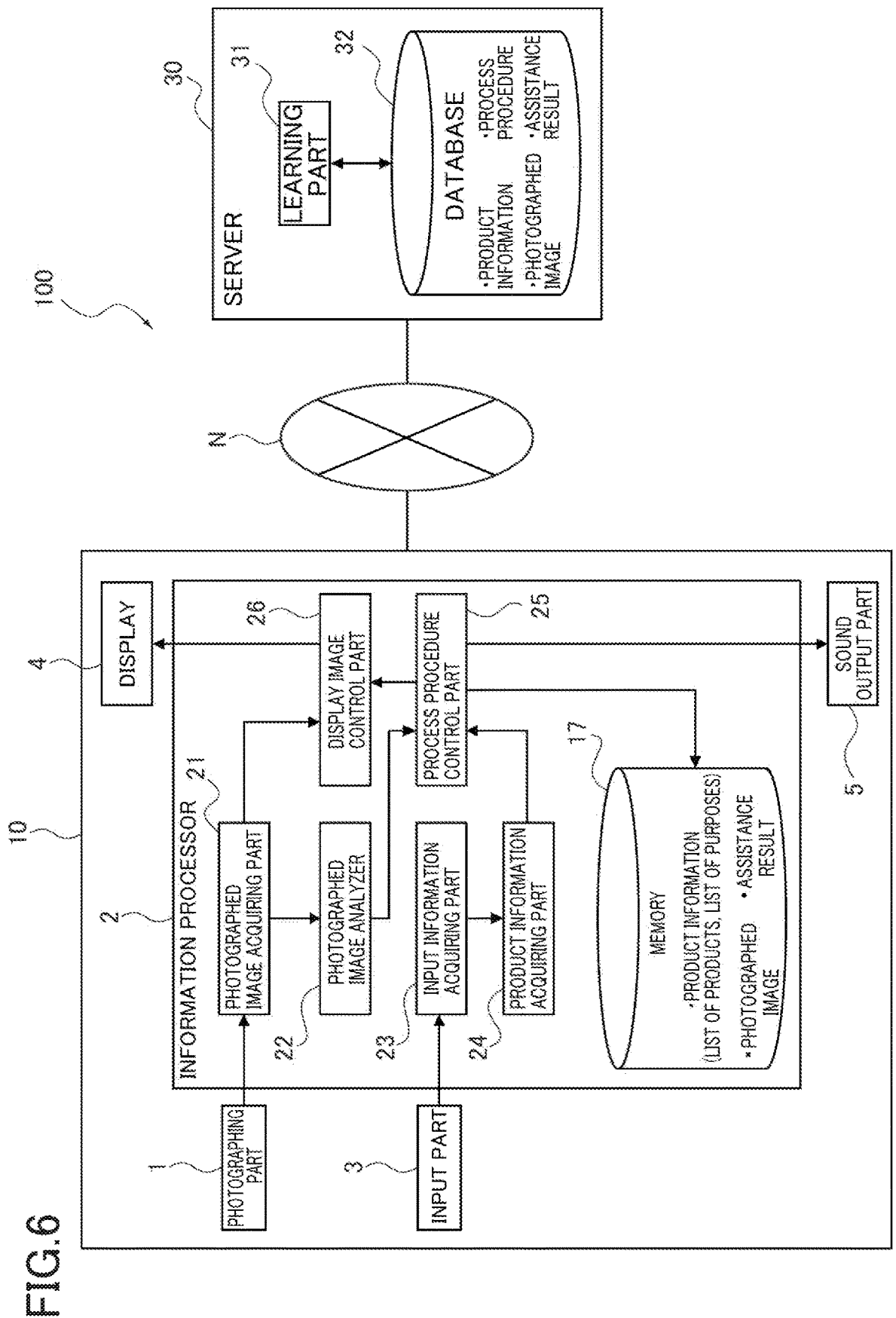
FIG. 6 is a functional block diagram of a dental treatment assistance system according to a fourth embodiment.

As illustrated in FIG. 6, the dental treatment assistance system 100 according to the fourth embodiment includes a dental treatment assistance device 10 arranged on a client side of a dental office and the like, and a server 30 managed by a manufacturer z who provides a dental treatment assistance service. The dental treatment assistance device 10 and the server 30 are connected via a communication network N such as the internet.

The dental treatment assistance system 100 includes at least one dental treatment assistance device 10. However, the dental treatment assistance system 100 preferably includes at plurality of dental treatment assistance devices 10 to be able to collect more assistance results of various cases, When the dental treatment assistance system 100 includes a plurality of the dental treatment assistance devices 10, one dental treatment assistance device 10 or a plurality of the dental treatment assistance devices 10 is/are provided in each of a plurality of dental offices, for example. Any of the dental treatment assistance devices 10A, 10B of the second and third embodiments may be provided in any of dental offices, for example, together with or instead of the dental treatment assistance device 10.

The dental treatment assistance device 10 of the fourth embodiment includes the basic configuration similar to the dental treatment assistance device 10 of the first embodiment except that the operation of each part and the information stored in the memory 17 differ in part from those in the first embodiment. Accordingly, the same reference numbers as those in the first embodiment are added to the components similar to those of the dental treatment assistance device 10 in the first embodiment, and thus the detailed description thereof will be omitted.

In the fourth embodiment, for example, the identification of the treatment step by the analysis of the photographed image and the selection of the product information and the process procedure to be displayed are performed by the server 30. The dental treatment assistance device 10 of the fourth embodiment sends the photographed image and the input information to the server 30 through the communication network N, and receives, for example, the treatment step, the process procedure, and the product information from the server 30 to perform the dental treatment assistance based on these. The detail of the operation of each part will be described with reference to the description of the operation using the flowchart of FIG. 7.

The server 30 is configured by a PC for a server including a CPU, a RAM, a ROM, a recording medium, and the like. However, for example, a large scale general purpose computer (mainframe) may be used. The PC for a server may use a cloud computing service, or may be a PC for an own server of a data center and a manufacture.

The server 30 mainly includes a learning part 31 and a database 32. In addition to these, the server 30 includes a general configuration and operation as the server 30, such as a communication part and an image display.

The database 32 stores the product information, the process procedure information, and various information items for use in object recognition. The database 32 also stores the photographed image, the assistance result and the like received from each dental treatment assistance device 10. The product information and the process procedure stored in the database 32 are successively updated (upgraded) by the rewriting with the learning part 31 or the provision of new information from a product distributor. The updated information may be sent to each dental treatment assistance device 10 in predetermined timing to be reflected in the memory 17.

The learning part 31 includes an artificial intelligence. The learning part 31 uses, as teaching data, data in which the feature amount representing a dental caries, a cavity, and a root canal of various conditions which require the treatment is associated with the actual treatment step, the process step, and the use material to the dental caries, the cavity, and the root canal of these various conditions, outputs the treatment step by using a mechanical learning algorithm based on the feature amount of the input photographed image, and outputs the preferable process step and use material. More advanced analysis and determination are thereby achieved. The learning part 31 acquires the product information and the process procedure information from the database 32 based on the input information received from each dental treatment assistance device 10, and sends the information to the dental treatment assistance device 10. The learning part 31 analyzes the photographed image sent from each dental treatment assistance device 10 with an object recognition technique to identify the treatment step, and sends the identified treatment step to the dental treatment assistance device 10. The learning part 31 may include an operation of distinguishing the performance state of each process step of a dental treatment (for example, application of dental material, air jet, and optical irradiation) to determine the display information, the sound information, and the like corresponding to the performance state, and of sending the determined information to the dental treatment assistance device 10.

The learning part 31 stores the product information of the use product, the process procedure information, the assistance result, and the like in the database 32. The learning part 31 acquires the product introduction information from the database 32 based on the assistance result, and sends the information to the dental treatment assistance device 10. The learning part 31 also analyzes the test result to be accumulated to arrive at a more suitable purpose and process procedure, and to be reflected on the process procedure and the like of the database 32.

One example of the dental treatment assistance process to be executed by the dental treatment assistance system 100 of the above configuration will be described with reference to the flowchart of FIG. 7 while clarifying differences from the respective parts of the first embodiment.

In response to the start of the dental treatment assistance program, the dental treatment assistance device 10 starts communicating with the server 30, receives the updated information from the server 30 when the product information and the process procedure information of the database 32 are updated, and updates the memory 17 (Step S20).

Next, in Step S21, the display image control part 26 displays the use purpose selection screen 41 (refer to FIG. 3) on the display 4. In Step S22, the input information acquiring part 23 acquires the information of the selected use purpose. In Step S23, according to the use purpose, the product information acquiring part 24 acquires a list of the product names from the memory 17. In Step S24, the display image control part 26 displays the use product selection screen 42 on the display 4 (refer to FIG. 3). In Step S25, the input information acquiring part 23 acquires the information of the use product.

In Step S26, the information processor 2 sends the input information to the server 30. The input information includes the photographed image acquired by the photographed image acquiring part 21, the acquired information of the use purpose, and the acquired information of use product. In Step S27, the learning part 31 of the server 30 analyzes the received photographed image to identify the treatment step while referring to the information of the use purpose and the input information on the use product. As the learning part 31 includes the artificial intelligence, the analysis can be performed with higher accuracy. In Step S28, the learning part 31 acquires the process procedure information including the information of the process procedure corresponding to the treatment step, the dental material, and the tool to be used in each step of the process procedure from the database 32.

Next, in Step S29, the server 30 sends the acquired process procedure information to the dental treatment assistance device 10. In the dental treatment assistance device 10 which has received this information, the display image control part 26 displays the real time photographed image on the photographed image display area 43a and displays the image of the dental material and the tool according to the treatment step on the material display area 43b to create the assistance screen 43 in which the process procedure according to the treatment step and the respective process steps are displayed to be displayed on the display surface 4a of the display 4 in Step S30. By visually recognizing the assistance screen 43, for example, a dental hygienist can confirm the treatment step, the necessary dental material, tool, and process procedure.

Next, in Step S31, the photographed image analyzer 22 analyzes the photographed image to determine whether or not the process has started. This determination may be made by the learning part 31 to enable the determination with higher accuracy. When the process has not been started (NO in Step S31), the program waits until the process starts. When it is determined that the process has started (YES in determination of Step S31), the process proceeds to Step S32, and the process procedure control part 25 counts the processing time and displays the counter image 43d when the counting of the processing time is required, and notifies the alarm in Step S33 when it reaches a time.

In the fourth embodiment, when a dentist performs the process with a time and a procedure different from the previously set processing time and procedure, the process procedure control part 25 stores the actual processing time and procedure, so that the information can be used as effective information when the learning part 31 of the server 30 analyzes the assistance result later on.

Next, in Step S34, when the process procedure control part 25 determines whether or not there is a next process step, and there is a process step (YES), the process returns to Step S26, the photographed image is sent to the server 30, the photographed image is analyzed in Step S27, the process procedure information is acquired in Step S28, the process procedure information and the like are sent to the dental treatment assistance device 10 in Step S29, the assistance screen 43 is displayed on the display 4 in Step S30, the performance of the process is determined in Step S31, the processing time is counted in Step S32 according to needs, and the alarm is notified in Step S33. The processes of these Step S26 to S33 are repeated until all the process steps are completed (until NO is determined in Step S34).

After that, the process proceeds to Step S35 to determine whether or not the treatment has been completed. When the treatment has not completed (NO), the process returns to Step S21, and the processes of Steps S21 to S34 are repeated for the next treatment step.

When the information processor 2 determines that the treatment has been completed in Step S35 (YES), the process procedure control part 25 stores the data in which the photographed image is associated with the assistance result of the use product, the use purpose, and the actual process procedure in the memory 17, and sends the data to the server 30. In the server 30, the data in which the received information is associated with, for example, the identification number of the dental treatment assistance device 10 is stored in the database 32 in Step S37, and the information is analyzed according to needs. Based on this analysis, the content of the process procedure may be changed to a more suitable content of the process procedure, for example, a more appropriate processing time of the drying and the optical irradiation may be set, and the process procedure information of the database 32 may be updated.

The process also proceeds to Step S38 according to needs, and the introduction information (refer to introduction information of first embodiment) of the product is extracted from the database 32, and the information is sent to the dental treatment assistance device 10. In Step S39, the display image control part 26 displays the received introduction information on the display 4 in the dental treatment assistance device 10.

In the server 30, the assistance results of a plurality of the dental treatment assistance devices 10 may be collected to be accumulated in the database 32, and the accumulated assistance results may be analyzed and studied by the learning part 31. The product to be preferably used by, for example, a dentist and the trend of the purpose can be thereby found out to be effectively used for a sales strategy, an improvement in a product, and a development in a new product.

As described above, in the dental treatment assistance system 100 of the fourth embodiment, with the dental treatment assistance device 10, the real time photographed image of the treatment target by the photographing part 1 and the process procedure corresponding to the use product and the use purpose are displayed on the display 4 visually recognized by a dentist and a dental hygienist, for example. With the learning part 31 having an artificial intelligence, the treatment step and the performance state can be identified in more detail and with higher accuracy. Accordingly, the dental treatment assistance system 100 which can accurately guide the process procedure corresponding to the treatment step, and can more appropriately assist the dental treatment without relying on a human memory can be provided.

With the connection between the server 30 and a plurality of the dental treatment assistance devices 10, the assistance results of various cases can be collected by the server 30. By analyzing the collected assistance results, the use condition of the product and the product preferred by a dentist and the like can be figured out, and the product and the use procedure more preferable for the treatment step can be considered to improve the product and develop the new product.

Fifth Embodiment

Next, as a fifth embodiment, a dental product sales promotion device and a dental product sales promotion method using the dental product sales prometon device will be described. The dental product sales promotion device of the fifth embodiment includes the dental treatment assistance device 10 of the first embodiment illustrated in FIG. 1 and a sales promotion part. In this embodiment, the process procedure control part 25 operates as the sales promotion part.

The sales promotion part (process procedure control part 25) includes an operation of displaying the information of the purchase site of the used product or the information of the purchase site of another product having the same purpose as the used product on the display 4 based on the assistance result of the dental treatment assistance device 10. In this embodiment, the process procedure control part 25 of the dental treatment assistance device 10 operates as the sales promotion part. However, the configuration is not limited thereto. As a modified example, a sales promotion part may be provided in addition to the process procedure control part 25, or the sales promotion part may be provided in a server connected via a communication network.

The dental material sales promotion method performed by the dental product sales promotion device of the above configuration displays, on the display 4, the information of the purchase site of the use product or the information of the purchase site of another product having the same use purpose based on the assistance result acquired by the method similar to the dental practice assistance method performed by the dental treatment assistance device 10 of the first embodiment. As such information of the purchase site, for example, the URL of the purchase site is displayed. The purchase site can be guided by clicking the URL, and thus, the sales promotion of the product which is required by a dentist and the like can be effectively performed.

As described above, the embodiments of this disclosure have been described in detail with reference to the drawings. However, the above embodiments are simple examples of this disclosure, and this disclosure is not limited to the configurations of the above embodiments. It is of course changes in a design are included in this disclosure without departing the gist of this disclosure.

The invention claimed is:

1. A dental treatment assistance device, comprising:
a display;
an input part into which input information on at least one of a use purpose and a use product is input, the input part being configured for inputting a character, a number, and/or an instruction, by dental personnel;
a memory that stores product information and process procedure information for a purpose of each product of a plurality of products;
a product information acquiring part that acquires the product information and the process procedure information corresponding to the input information input from the input part;
an information processor comprising a learning part having an artificial intelligence;
a display image control part that displays a predetermined process procedure selected from the process procedure information on the display, the information comprising instructions on a first use for a first product or for a second use instruction of a second product, the second product having the same purpose as the first product, to apprise a dentist and a dental hygienist of a procedure of the first use of the first product, a second use of the first product, and a more appropriate second product for the same purpose;
a photographing part that photographs an oral cavity of a person to be treated including a treatment target;
a process procedure control part that stores an association between a photographed image by the photographing part and an assistance result in memory; and
a photographed image analyzer that analyzes the photographed image from a photographed image accruing part to detect a treatment target that comprises at least one selected from a dental caries, a cavity, and a root canal,
wherein the assistance result comprises the input information, the product information, the process procedure, and a performance result of the process procedure, and
wherein the photographed image analyzer analyzes the photographed image to thereby identify a treatment by a dentist based on an analysis result and the input information,
wherein the information of a detected treatment target and the information of a recognized treatment are sent to the process procedure control part,
wherein the information processor is configured to perform a more detailed advanced treatment assistance based on the information analyzed by the photographed image analyzer and previously stored teaching data,
wherein the photographed image analyzer identifies the treatment target by the image analysis, and inputs a feature amount and the input information of the treatment target to the learning part,
wherein the learning part uses, as teaching data, data in which the feature amount presenting the dental caries, cavity, and/or root canal, of various conditions which require a treatment is associated with an actual treatment, process, and the product information to be used, to the dental caries, the cavity, the root canal.

2. The device of claim 1, wherein the display is provided in a head mount display, and the display has a permeability to enable visual recognition of a treatment target while displaying the process procedure.

3. The device of claim 1, wherein the process procedure control part further counts a processing time when a performance of a predetermined step of the process procedure is detected, and notifies an alarm when it reaches a processing time.

4. The device of claim 1, wherein the process procedure control part further notifies the process procedure with sound.

5. The device of claim 1, wherein the process procedure control part further stores an assistance result including the input information, the product information, the process procedure, and a performance result of the process procure in the memory.

6. The device of claim 5, wherein the process procedure control part further displays introduction information of a product used or introduction information of a product corresponding to the process procedure on the display based on the assistance result.

7. The device of claim 1, wherein the display image control part displays a predetermined process procedure selected from the process procedure information and a photographed image by the photographing part side by side on the display.

8. The device of claim 1, wherein the product information comprises a product name, a name of a dental material contained in a product, a component of each dental material, a usable purpose, and/or information on a tool and a device for use in each purpose.

9. The device of claim 1, wherein the display is provided in a head mount display, and the display has a permeability to enable visual recognition of a treatment target while displaying the process procedure, and
wherein the product information comprises a product name, a name of a dental material contained in a product, a component of each dental material, a usable purpose, and/or information on a tool and a device for use in each purpose.

10. The device of claim 1, further comprising:
a process procedure control part that counts a processing time when a performance of a predetermined step of the process procedure is detected, and notifies an alarm when it reaches a processing time; and
a process procedure control part that notifies the process procedure with sound.

11. The device of claim 1, further comprising:
a process procedure control part that counts a processing time when a performance of a predetermined step of the process procedure is detected, and notifies an alarm when it reaches a processing time; and
a process procedure control part that notifies the process procedure with sound,
wherein the product information comprises a product name, a name of a dental material contained in a product, a component of each dental material, a usable purpose, and/or information on a tool and a device for use in each purpose.

12. The device of claim 1, further comprising:
a process procedure control part that counts a processing time when a performance of a predetermined step of the process procedure is detected, and notifies an alarm when it reaches a processing time,
wherein the photographing part provides photographic information comprising a photographed image,
wherein the display image control part displays a predetermined process procedure selected from the process procedure information and the photographed image by the photographing part side by side on the display,
wherein the display is provided in a head mount display, and the display has a permeability to enable visual recognition of a treatment target while displaying the process procedure,
wherein the product information comprises a product name, a name of a dental material contained in a product, a component of each dental material, a usable purpose, and/or information on a tool and a device for use in each purpose, and
wherein the photographed image analyzer is configured to detect completion of a drying process.

13. The device of claim 12, wherein the display displays to the dental personnel each process step of a dental treatment.

14. The device of claim 13, wherein the product comprises a bond, a cement, a filling composite resin, a composite resin for constructing an abutment, a metal alloy, ceramics, a resin hardened material, a plaster material, a burying agent, a grinding agent, and/or an adhesive, and
wherein the display further displays materials information comprising the dental material, tool, and/or processing procedure for the dental treatment.

15. The device of claim 1, wherein the photographed image is displayed on the display in real time by the display image control part.

16. The device of claim 1, wherein the display image control part displays the acquired photographed image on the photographed image display area, displays the images of the dental material, and the tool to be used on the material display area.

17. The device of claim 1, further comprising:
an assistance screen,
wherein the assistance screen displays the image of the process procedure on a process procedure display area on a display surface of the display.

18. A dental treatment assistance system, comprising:
the dental treatment assistance device of claim 1; and
a server that is connected with the dental treatment assistance device through a communication network,
wherein the dental treatment assistance device further comprises:
an information processor that sends a photographed image by the photographing part and the input information input from the input part to the server,
wherein the server comprises:
a learning part having an artificial intelligence; and
a memory that stores product information and process procedure information for a purpose of each product of a plurality of products,
wherein the learning part is configured to acquire the photographed image and the input information through the communication network from the dental treatment assistance device, identify a treatment by analyzing the photographed image, and acquire the process procedure information corresponding to the treatment from the memory based on the identified treatment and the input information to be sent to the dental treatment assistance device, and
wherein the information processor of the dental treatment assistance device displays the photographed image and the process procedure information acquired from the learning part on the display.

19. A dental treatment assistance method that is performed by the dental treatment assistance device of claim 1, the method comprising:
acquiring the product information corresponding to the input information input from the input part and the process procedure information from the memory; and
displaying a predetermined process procedure selected from the process procedure information on the display.

20. A non-transitory computer readable storage medium, with a program causing the dental treatment device of claim 1 to function as:
storing product information of a plurality of products and process procedure information;
acquiring a photographed image of an oral cavity of a person to be tested including a treatment target;
acquiring input information on at least one of a use purpose and a use product;
acquiring the product information corresponding to the input information and the process procedure information from the storage; and
displaying a predetermined process procedure selected from the process procedure information and the photographed image side by side on the display.

21. A dental product sales promotion device, comprising:
the dental treatment assistance device of claim 1; and
a sales promotion part that displays information of a purchase site of a used product or information of a purchase site of another product having a same purpose as the used product on the display.

* * * * *